United States Patent
Weldon et al.

(10) Patent No.: US 9,750,483 B2
(45) Date of Patent: Sep. 5, 2017

(54) CYTOLOGY BRUSH DEVICES AND METHODS OF USE

(71) Applicant: Boston Scientific Scimed, Inc., Maple Grove, MN (US)

(72) Inventors: James Weldon, Newton, MA (US); Larry E. Stanton, Burlington, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 232 days.

(21) Appl. No.: 14/303,953

(22) Filed: Jun. 13, 2014

(65) Prior Publication Data

US 2015/0005665 A1    Jan. 1, 2015

Related U.S. Application Data

(60) Provisional application No. 61/839,633, filed on Jun. 26, 2013.

(51) Int. Cl.
*A61B 1/32* (2006.01)
*A61B 10/02* (2006.01)
*A61B 1/00* (2006.01)

(52) U.S. Cl.
CPC .......... *A61B 10/02* (2013.01); *A61B 1/00131* (2013.01); *A61B 2010/0216* (2013.01)

(58) Field of Classification Search
CPC . A61B 10/0096; A61B 10/02; A61B 10/0291; A61B 10/04; A61B 2010/0216; A61B 2017/32001; A61B 2017/320012; G01N 2001/028; B01L 3/5029; A46B 9/02; A46B 9/021; A46B 9/025; A46B 9/028

See application file for complete search history.

(56) References Cited

U.S. PATENT DOCUMENTS

| | | | |
|---|---|---|---|
| 3,881,464 A | 5/1975 | Levene | |
| 3,945,372 A | 3/1976 | Milan et al. | |
| 4,227,537 A * | 10/1980 | Suciu | A61B 10/0291 600/569 |
| 4,235,244 A | 11/1980 | Abele et al. | |
| 4,762,133 A | 8/1988 | Bayne et al. | |
| 4,850,957 A | 7/1989 | Summers | |
| 4,966,162 A | 10/1990 | Wang | |
| 4,981,143 A * | 1/1991 | Sakita | A61B 10/0291 600/570 |
| 5,217,023 A | 6/1993 | Langdon | |
| 5,713,369 A * | 2/1998 | Tao | A61B 10/0291 600/569 |

(Continued)

*Primary Examiner* — Sean Dougherty
*Assistant Examiner* — Patrick Fernandes
(74) *Attorney, Agent, or Firm* — Seager, Tufte & Wickhem, LLP (57) ABSTRACT

According to one aspect of the present disclosure, a cytology brush may include an elongated shaft including a proximal end portion and a distal end portion. The cytology brush may also include a plurality of bristles mounted on the distal end portion of the elongated shaft. The plurality of bristles may be arranged at least partially around the distal end portion of the elongated shaft, and may be configured to engage tissue. An outer surface of at least one of the bristles may include a micropattern formed by a plurality of protrusions or recesses. The plurality of protrusions or recesses may be separated by one or more gaps.

16 Claims, 4 Drawing Sheets

(56) References Cited

U.S. PATENT DOCUMENTS

| | | | |
|---|---|---|---|
| 6,193,674 B1* | 2/2001 | Zwart | A61B 10/0291 |
| | | | 600/569 |
| 8,323,211 B2* | 12/2012 | Larkin | A61B 10/0045 |
| | | | 600/562 |
| 8,795,197 B2 | 8/2014 | Lonky et al. | |
| 2007/0282222 A1* | 12/2007 | Larkin | A61B 10/0045 |
| | | | 600/569 |
| 2008/0313838 A1* | 12/2008 | Nakatani | A61F 11/006 |
| | | | 15/236.01 |
| 2009/0062691 A1* | 3/2009 | Kim | A61B 10/0291 |
| | | | 600/569 |
| 2014/0088459 A1* | 3/2014 | Roush | A61M 25/0032 |
| | | | 600/569 |

* cited by examiner

CYTOLOGY BRUSH DEVICES AND METHODS OF USE

CROSS-REFERENCE TO RELATED APPLICATIONS

This application claims the benefit of priority of U.S. Provisional Application No. 61/839,633, filed Jun. 26, 2013, the entirety of which is incorporated by reference herein.

DESCRIPTION OF THE DISCLOSURE

Field of the Disclosure

Embodiments of the present disclosure generally relate to medical devices and related methods of use. In particular, embodiments of the present disclosure relate to cytology brushes for use in various medical procedures.

Background of the Disclosure

Certain medical tests require sampling of cells from target areas of a subject's body. For instance, a screening test for detecting potentially pre-cancerous and cancerous tissues in a subject's body, may include taking samples of cells from a target area of the subject's body. A cytology brush may be used to collect cells from the target area.

The cytology brush may include multiple bristles arranged on a shaft. The bristles may brush or rub against the target area, agitating the target area, and thereby scraping cells off of tissue in the target area. The cells may be trapped between the bristles. However, during removal of the brush from the target area and the subject's body, the bristles may be disturbed, possibly causing the captured cells to disengage from the bristles. Cells may also be scraped off the bristles by structures that come into contact with the bristles. Hence, the number of cells retrieved for analysis may be reduced.

It may therefore be beneficial to provide a cytology device with an enhanced cell capture and retrieval rate.

SUMMARY

The present disclosure describes a medical device for capturing cells from a subject's body.

According to one aspect of the present disclosure, a cytology brush may include an elongated shaft including a proximal end portion and a distal end portion. The cytology brush may also include a plurality of bristles mounted on the distal end portion of the elongated shaft. The plurality of bristles may be arranged at least partially around the distal end portion of the elongated shaft, and may be configured to engage tissue. An outer surface of at least one of the plurality of bristles may include a micropattern formed by a plurality of protrusions or recesses. The plurality of protrusions or recesses may be separated by one or more gaps.

According to another aspect of the present disclosure, a medical device may include a cytology brush. The cytology brush may include an elongated shaft including a proximal end portion and a distal end portion. The cytology brush may also include a plurality of bristles mounted on the distal end portion of the elongated shaft. The plurality of bristles may be arranged at least partially around the distal end portion of the elongated shaft. The plurality of bristles may be configured to engage tissue. An outer surface of at least one of the bristles may include a micropattern formed by a plurality of protrusions or recesses. The plurality of protrusions or recesses may be separated by one or more gaps. The medical device may also include a sheath having a central lumen and a distal end opening. The central lumen may be configured to receive at least a portion of the cytology brush, and at least a portion of the cytology brush may be configured to pass through the distal end opening.

According to another aspect of the present disclosure, a dilator may be configured to dilate an opening in a body. The dilator may include an elongated shaft including a proximal end portion and a distal end portion. The dilator may also include a micropatterned region arranged at least partially around the distal end portion of the elongated shaft. The micropatterned region may be configured to engage tissue surrounding the opening, and dilate the opening. The micropatterned region may include a plurality of protrusions or recesses, separated by one or more gaps.

Additional characteristics, features, and advantages of the described embodiments will be set forth in part in the description that follows, and in part will be apparent from the description, or, may be learned by practicing the disclosure. The disclosed subject matter can be realized and attained by way of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The accompanying drawings, which are incorporated in, and constitute a part of this specification, illustrate exemplary embodiments of the present disclosure and, together with the description, serve to explain the principles of the disclosure.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts.

The present disclosure describes medical devices for capturing cells from a target area of a subject's body. The medical device may include one or more portions with micropatterns disposed on an outer surface thereof, to engage and retain cells at the target area.

Figure 1:
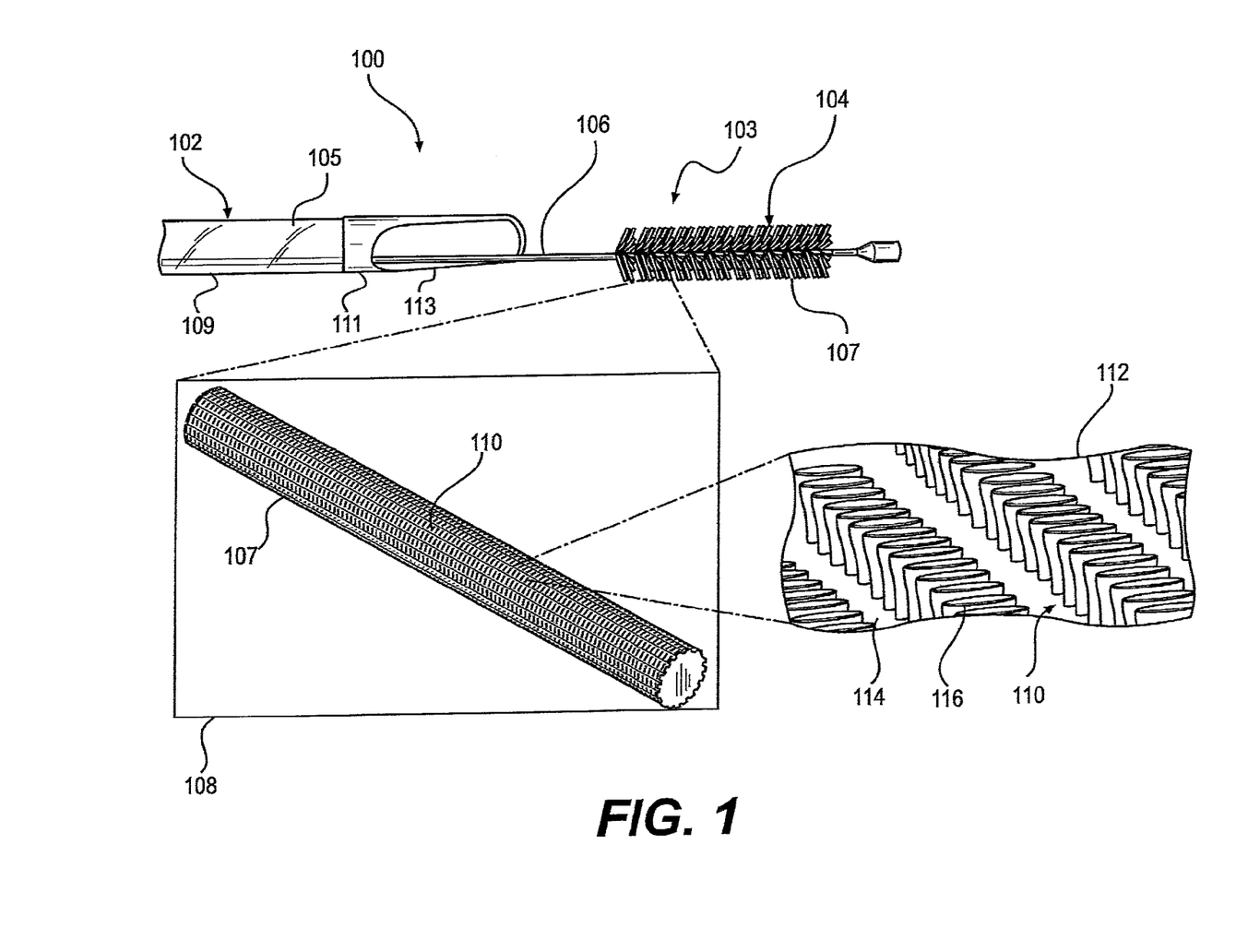
FIG. 1 shows a side view, and close-up views, of an exemplary embodiment of a medical device, according to an aspect of the present disclosure.

FIG. 1 is a side view of one embodiment of a medical device 100. The medical device 100 may include an introduction sheath 102, such as a catheter or other tubular member. The medical device 100 may also include a cytology brush 103 including a shaft 106, and a plurality of bristles 104 disposed on a distal portion of the shaft 106. The sheath 102 may include a central lumen 105 configured to slidably receive the brush 103.

The sheath 102 may include an elongated member 109 having a proximal portion (not shown) positionable outside of a subject's body, and a distal portion configured for insertion into and navigation through the subject's body. The sheath 102 may also include a tip member 111 coupled to a distal end of the elongated member 109. The tip member 111 may have a tapered distal end portion with an atraumatic or rounded distal tip, to aid in insertion of the sheath 102 into the subject's body, and navigation of the sheath 102 through the subject's body. The tip member 111 may also include an opening 113, through which the cytology brush 103 may be extended and retracted.

In one embodiment, the elongated member 109 may have a substantial circular cross-section. However, in other embodiments, the elongated member 109 may have a triangular, square, ovoid, rectangular, and/or any other suitably shaped cross-section. It is contemplated that the characteristics of the sheath 102 may vary depending upon the subject's anatomy and/or the type of procedure being performed.

In some embodiments, outer surfaces of the elongated member 109 and/or the tip member 111 may be coated with a lubricious material, such as Teflon, polyvinylchloride, or the like, to reduce friction between the outer surfaces and any surfaces coming into contact with the outer surfaces. This may reduce the force needed to insert the sheath 102, and direct movement of the sheath 102. It is contemplated that the sheath 102 may be inserted through a lumen of an outer sheath (not shown), such as an endoscope, bronchoscope, laryngoscope, or the like.

The lumen 105 may extend longitudinally through the elongated member 109, and may slidably receive the cytology brush 103. During insertion of the medical device 100 into the subject's body, or withdrawal of the medical device 100 from the subject's body, the cytology brush 103 may be in a retracted position, with the shaft 106 pulled proximally to position the bristles 104 within the lumen 105. The shaft 106 of the cytology brush 103 may be pushed distally to move the cytology brush 103 to an extended position (shown in FIG. 1), with the bristles 104 extending out of the distal opening 113, so they are exposed from the sheath 102.

The shaft 106 may include one or more wires twisted into an elongated form. The bristles 104 may be clamped between the twisted wires, or otherwise mounted on the shaft 106. The shaft 106 may have sufficient flexibility to allow it to bend during insertion of the cytology brush 103 into or withdrawal of the cytology brush 103 from the subject's body. The shaft 106 may have sufficient rigidity so that pushing or pulling of the shaft 106 may cause extension or retraction, respectively, of the cytology brush 103 from the sheath 102. A proximal portion (not shown) of the shaft 106 may be gripped by a user such that the user may manually push or pull the shaft 106. Dimensions of the shaft 106 may vary depending upon the subject's anatomy, and/or the type of procedure being performed.

The bristles 104 may be employed to brush against a tissue surface in the target area to capture cells. The bristles 104 may be arranged/mounted around the distal portion of the shaft 106. In some embodiments, each of the bristles 104 may have a cross-section that is substantially circular. However, the bristles 104 may have any other suitable cross-sectional shape, including rectangular, triangular, square, polygonal, elliptical, or oblong.

The bristles 104 may be made of one or more filaments. For example, a plurality of the bristles 104 may be made of a continuous length of a filament. Alternatively, a plurality of the bristles 104 may be made of separate lengths of a filament. The filament may be a monofilament. The monofilmant may be formed by extrusion. Alternatively, the filament may be a multicomponent filament. A multicomponent filament may include a core about which one or more layers of material are concentrically arranged. If multiple layers are present, they may differ in composition and/or thickness. The outermost one of the layers may include micropatterning, as will be described in more detail below. The multicomponent filament may be formed by coextrusion. It is contemplated that the filament may be made of nylon, polymer, and/or any suitable material or combination of materials.

The bristles 104 may be arranged helically around the distal portion of the shaft 106, and may extend radially outwards from the shaft 106. In some embodiments, the bristles 107 may radiate at an angle relative to the longitudinal axis of the shaft 106. When the bristles 104 are brushed against tissue in the target area, cells from the tissue may be transferred to the bristles 104, and may be captured between the bristles 104.

A close-up view 108 of one bristle 107 is shown in FIG. 1. While a single bristle 107 is shown in the close-up view 108, it should be understood that some or all of the bristles 104 may include the same features as the bristle 107. An outer surface of the bristle 107 may include a micropattern 110. The micropattern 110 may include a plurality of microstructures, such as protrusions 116, extending radially outwardly from the outer surface of the bristle 107. The protrusions 116 are shown in a close-up view 112 of a portion of the bristle 107. The protrusions 116 may be cylindrical in one embodiment, with a circular cross-sectional shape, but it should be understood that the protrusions 116 may have any other suitable shape. For example, the protrusions 116 may have a rectangular, oval, elliptical, oblong, spherical, triangular, hexagonal, or irregular cross-sectional shape.

The protrusions 116 may be spaced from each other to define a gap or space 114 between adjacent protrusions 116. Cells, or portions thereof, may enter the gap 114, and may be held therein by engagement with the protrusions 116 on each side of the gap 114. In some embodiments, the gap 114 may have a length in the range of 10-20 micrometers, and the protrusions 116 may have a width of between 10 and 20 micrometers. The dimensions of the gap 114 and the protrusions 116 may vary, however, based on the type of cells a user wants to capture.

The gaps 114 and/or the protrusions 116 may be configured to be arranged in an array of rows and columns around the bristle 107, thereby forming the micropattern 110. However, the gaps 114 and/or the protrusions 116 may be arranged in other configurations, including, but not limited to, circumferential rings or bands, spiral-shaped regions, zig-zag shaped regions, criss-crossing regions, a diagonal pattern of gaps 114 and/or protrusions 116, a staggered pattern, a random or irregular pattern, and/or any other suitable pattern or configuration, or combination of patterns or configurations. The protrusions 116 and/or gaps 114 may be formed on the outer surface by, for example, micromachining. It is also contemplated that they may be formed during extrusion/coextrusion of the filament.

Figure 4:
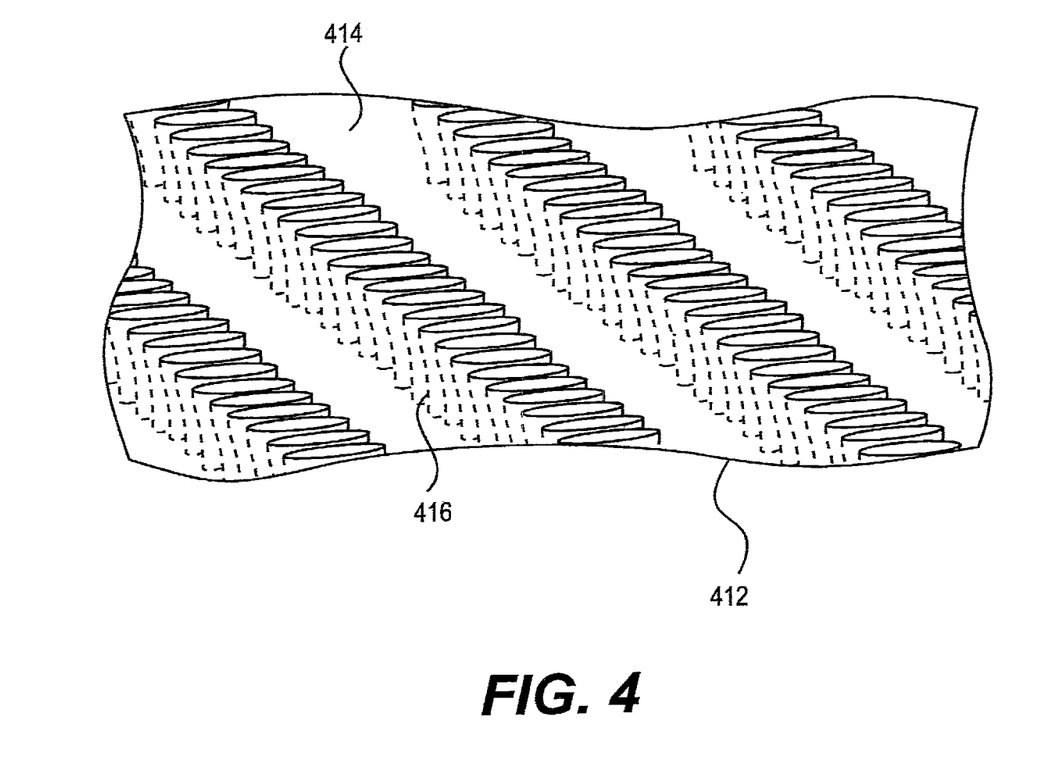
FIG. 4 is a close-up view of an exemplary embodiment of a micropattern, according to an aspect of the present disclosure.

Additionally or alternatively, the micropattern 110 may include one or more microstructures, such as microholes or recesses, extending radially inwardly from the outer surface of the bristle 107. The recesses 416 are shown in a close-up view 412 of a portion of the bristle 107 (FIG. 4). The recesses 416 may be cylindrical in one embodiment, with a circular cross-sectional shape, but it should be understood that the recesses 416 may have any other suitable shape. For example, the recesses 416 may have a rectangular, oval, elliptical, oblong, spherical, triangular, hexagonal, or irregular cross-sectional shape. The recesses 416 may also have a suction cup shape, with one or more curved surfaces. When one or more of the suction cup recesses 416 comes into contact with a cell, the volume of space between the recess 416 and a surface of the cell may be reduced. Fluid (such as air and/or a liquid) may be expelled past a rim of the recess 416. Negative fluid pressure may develop in the recess, and may promote adhesion of the cell to the bristle 107.

The recesses 416 may be spaced from each other to define a gap or space 414 between adjacent recesses 416. The gap 414 may be formed by material forming the bristle 107. Cells, or portions thereof, may enter the recesses 416, or may be held to the recesses 416 by suction, keeping the cells in engagement with the bristle 107. In some embodiments, the gap 414 may have a length in the range of 10-20 micrometers, and the recesses 416 may have a width of between 10 and 20 micrometers. The dimensions of the gap 414 and the recesses 416 may vary, however, based on the type of cells a user wants to capture.

The gaps 414 and/or the recesses 416 may be configured to be arranged in an array of rows and columns around the bristle 107, thereby forming the micropattern 110. However, the gaps 414 and/or the recess 416 may be arranged in other configurations, including, but not limited to, circumferential rings or bands, spiral-shaped regions, zig-zag shaped regions, criss-crossing regions, a diagonal pattern of gaps 414 and/or recesses 416, a staggered pattern, a random or irregular pattern, and/or any other suitable pattern or configuration, or combination of patterns or configurations. The recesses 416 and/or gaps 414 may be formed on the outer surface by, for example, micromachining.

A source of electrical energy (not shown) may be coupled to the proximal portion of the medical device 100. The electrical energy source may be configured to supply electrical current to the bristles 104 through the shaft 106. The electrical current may provide an electrical charge to the bristles 104, thereby changing one or more characteristics of the bristles 104. For example, the electrical current may change a static charge on the bristles 104, to increase or decrease the gripping force between the cells and the bristles 104, and/or to increase or decrease attraction/repulsion forces between the protrusions 116, to cause them to move towards each other, or away from each other.

An exemplary method of using the medical device 100 is outlined below. The sheath 102 may be inserted into the subject's body through an incision or a natural orifice, and may be navigated to a target area of the subject's body. For example, an outer sheath (not shown), such as an endoscope, may be inserted into the subject's body and navigated through the subject's body until a distal end of the outer sheath reaches the target area. The sheath 102 may be inserted through a lumen of the outer sheath, and a pushing force on a proximal portion of the sheath 102 may be used to direct the sheath 102 through the lumen of the outer sheath, toward the distal end of the outer sheath. Alternatively, the sheath 102 may be prepositioned within the outer sheath prior to insertion of either into the subject's body, and the sheath 102 and the outer sheath may be inserted into the subject's body and navigated to the target area together.

The cytology brush 103 may be inserted into the sheath 102 at any time before, during, or after the sheath 102 has been inserted into the outer sheath. By pushing on a proximal end portion of the shaft 106, the user may position the bristles 104 near the opening 113 in the tip member 111.

Once the outer sheath, sheath 102, and cytology brush 103 are in position at the target area, the cytology brush 103 may be extended from within the sheath 102 and the outer sheath, to expose the bristles 104. This step may also include extending the sheath 102 out from within the outer sheath. It is contemplated that positioning of the outer sheath, sheath 102, and cytology brush 103 may be monitored using an imaging device (not shown) positioned at a distal end of the outer sheath.

The bristles 104 may be moved into contact with tissue in the target area. For example, the proximal end of the shaft 106 may be pushed and/or pulled, thereby causing the bristles 104 to move backward and/or forward on the tissue surface. The bristles 104 may brush against the tissue, thereby scraping off cells from the tissue. The cells may be held between bristles 104. Additionally or alternatively, the cells may be held between protrusions 116 on one or more of the bristles 104, or by recesses 416 on one or more of the bristles 104.

Once the brushing step has been completed, the proximal portion of the shaft 106 may be pulled to cause the bristles 104 to move back towards and into the distal opening 113. Once retracted, the bristles 104, and the cells thereon, may be kept out of contact with other parts of the subject's body, during removal of the medical device 100 from the target area. The captured cells may be collected for analysis by separating them from the bristles 104. This process may include rinsing the bristles 104 with a fluid to free the cells. Additionally or alternatively, the process may include activating the electrical energy source to cause the cells to be released or repelled from the bristles 104, cause the protrusions 116 to move apart, thereby loosening their hold on the cells, and/or deform or expand the recesses 416 to loosen their hold on the cells by, for example, breaking suction.

Figures 2A, 2B:
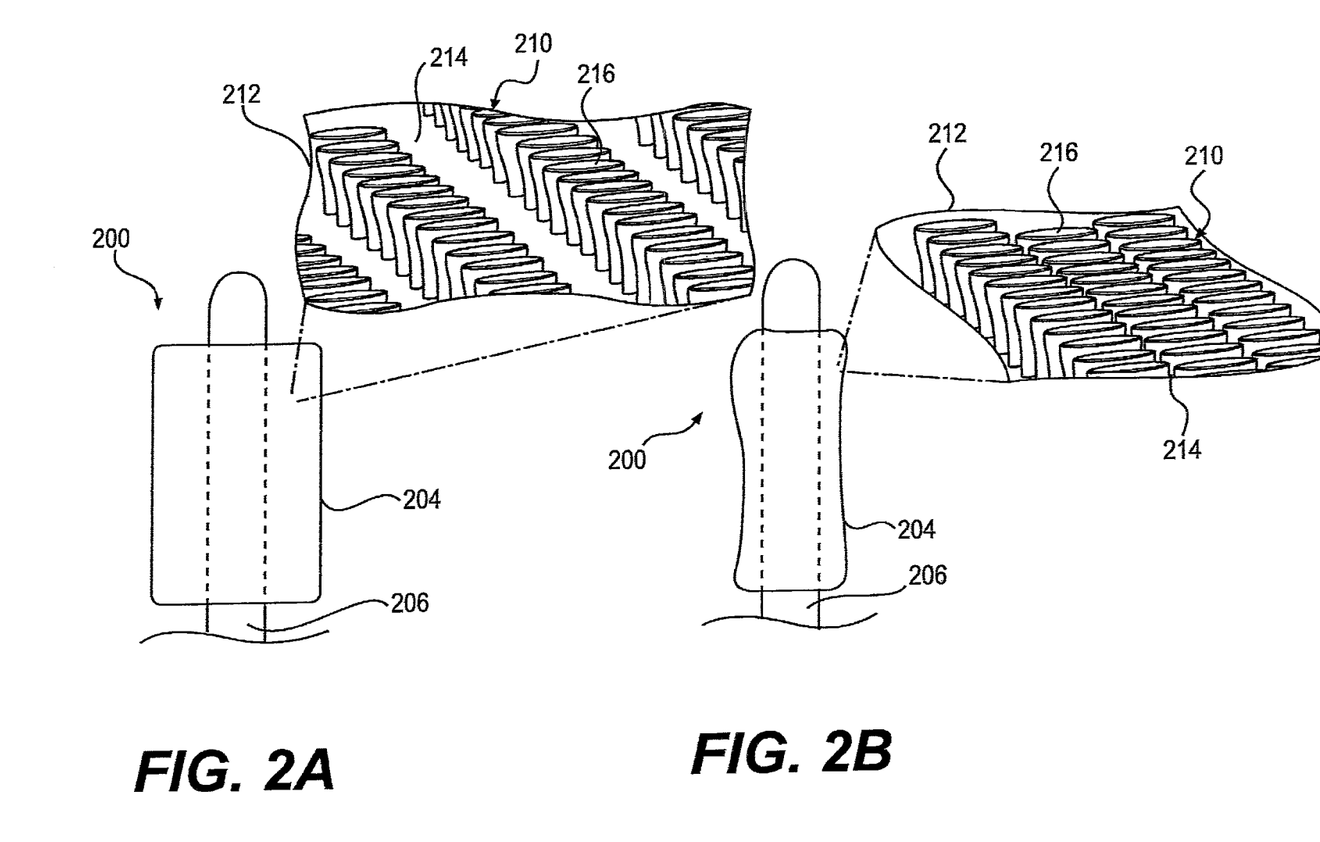
FIG. 2A is a schematic top view, and a close-up view, of an exemplary embodiment of a medical device in an expanded state, according to an aspect of the present disclosure.
FIG. 2B is a schematic top view, and a close-up view, of the medical device of FIG. 2A in an unexpanded state, according to an aspect of the present disclosure.

FIGS. 2A and 2B are schematic top views of a dilator 200. The dilator 200 may be inserted into a subject's body, and navigated to a target area. For example, the dilator 200 may be positioned in the target area in a manner similar to the way the medical device 100 is positioned in the target area.

The dilator 200 may include an elongated shaft 206, and an expandable member 204 mounted on a distal portion of the shaft 206. The expandable member 204 may extend circumferentially around the distal portion of the shaft 206. The expandable member 204 may include a balloon configured to inflate to dilate an opening in the subject's body, and deflate to make it easier to move the dilator 200 to the target area. The expandable member 204 may be made of an elastic material that may stretch/deform when expanded by an expanding force, and may return to its original form when the expanding force is removed.

FIG. 2A shows the expandable member 204 in an expanded/inflated state, while FIG. 2B shows the expandable member 204 in an at least partially unexpanded/deflated state. It is contemplated that the outer surface of the expandable member 204 may be substantially flush with the outer surface of the shaft 206 when the expandable member 204 is in a fully unexpanded/deflated state. It is also contemplated that the shaft 206 may include one or more longitudinally extending lumens (not shown) coupled to a pump or similar device (not shown), for inflating and deflating the expandable member 204 with a fluid.

The outer surface of the expandable member 204 may include a micropattern 210. The micropattern 210 may include protrusions 216 on the outer surface of the expandable member 204, and gaps 214 between the protrusions

216. The protrusions 216 and gaps 214 are shown in the enlarged view 212. The micropattern 210, gaps 214, and protrusions 216 may be similar to the micropattern 110, gaps 114, and protrusions 116 of the medical device 100.

When the expandable member 204 is placed within the opening, and is expanded/inflated to dilate the opening, the outer surface of the expandable member 204 may press against, rub against, or otherwise contact tissue around the opening. As a result, cells from the tissue may transfer onto the outer surface of the expandable member 204. The expansion/inflation may also increase the size of the gaps 214. Cells, or portions thereof, may be received in the enlarged gaps 214. Once the dilation steps has been completed, the expandable member 204 may be deflated or otherwise allowed to return to its unexpanded state. As such, the size of the gaps 214 may decrease. As the gaps 214 become smaller, and the protrusions 216 move closer together, they may exert a clamping force on the cells, or portions of the cells, transferred onto the outer surface of the expandable member 204. The clamping force may help retain the cells on the dilator 200. Thus, the dilator 200 may fulfill the role of a dilator and the role of a cytology brush. By accomplishing multiple tasks with the same device 300, procedures requiring dilation and analysis of cells may be performed with greater efficiency.

Additionally or alternatively, the micropattern 210 may include recesses on the outer surface of the expandable member 204, and gaps between the recesses. Exemplary recesses 416 and gaps 414 are shown in the enlarged view 412 (FIG. 4), and their characteristics have been described above.

When the expandable member 204 is placed within the opening, and is expanded/inflated to dilate the opening, the outer surface of the expandable member 204 may press against, rub against, or otherwise contact tissue around the opening. As a result, cells from the tissue may transfer onto the outer surface of the expandable member 204. The expansion/inflation may also increase the size of the recesses 416. Cells, or portions thereof, may be received in the enlarged recesses 416. Once the dilation steps has been completed, the expandable member 204 may be deflated or otherwise allowed to return to its unexpanded state. As such, the size of the recesses 416 may decrease. As the recesses 416 become smaller, walls of the recesses 416 may exert a clamping force on the cells, or portions of the cells, transferred onto the outer surface of the expandable member 204. The clamping force may help retain the cells on the dilator 200. Additionally or alternatively, as the recesses 416 become smaller, fluid (such as air and/or a liquid) may be expelled past a rim of the recesses 416. Negative fluid pressure may develop/increase in the recesses 416, and may promote adhesion (e.g., by suction) of cells to the expandable member 204. Thus, the dilator 200 may fulfill the role of a dilator and the role of a cytology brush. By accomplishing multiple tasks with the same device 300, procedures requiring dilation and analysis of cells may be performed with greater efficiency.

A source of electrical energy (not shown) may be coupled to the proximal portion of the medical device 200. The electrical energy source may be configured to supply electrical current to the expandable member 204 through the shaft 206. The electrical current may provide an electrical charge to the expandable member 204, thereby changing a static charge on the expandable member 204, to increase or decrease the gripping force between the cells and the expandable member 204. Additionally or alternatively, the electrical current may increase or decrease attraction/repulsion forces between the protrusions 216, to cause them to move towards each other, or away from each other. Additionally or alternatively, the electrical current may deform the recesses 416, and may result in a decrease in clamping and/or suction forces exerted on cells by the recesses 416.

Figure 3:
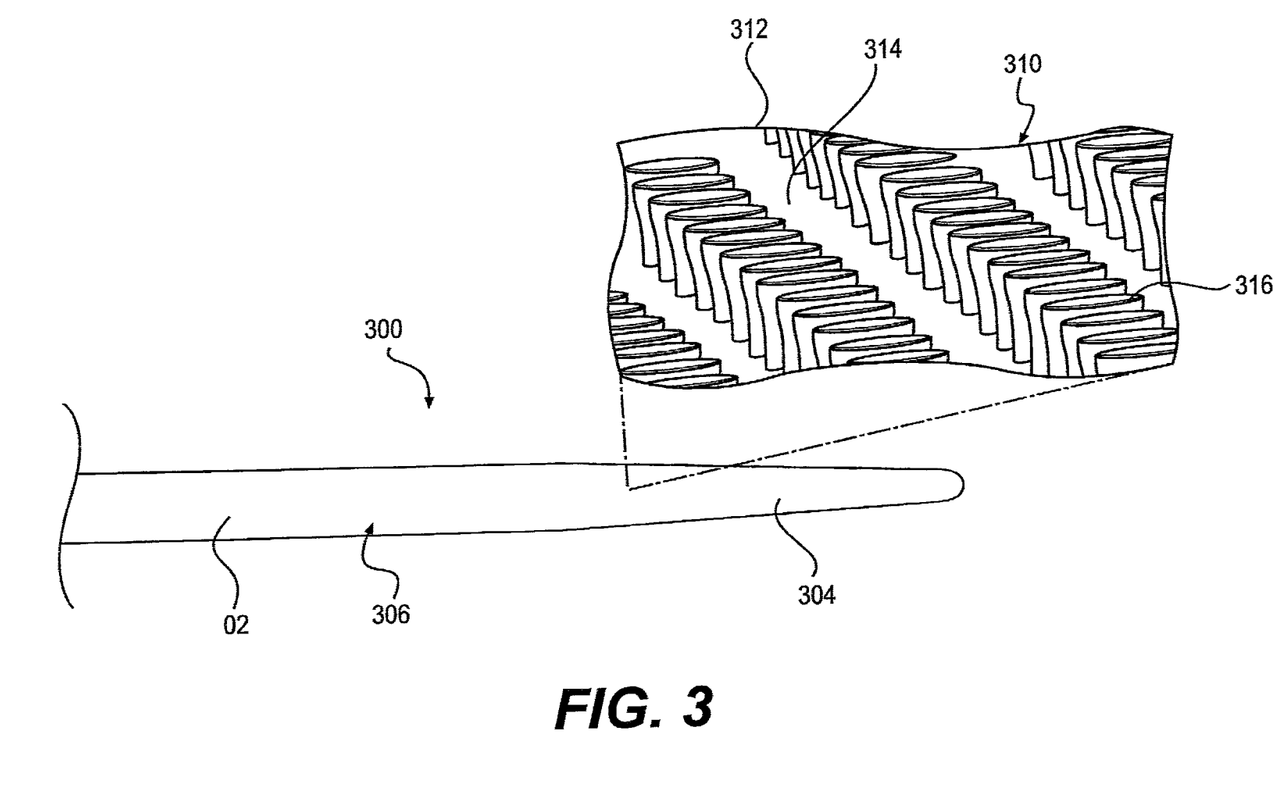
FIG. 3 is a side view, and a close-up view, of an exemplary embodiment of a medical device, according to an aspect of the present disclosure.

FIG. 3 is a side view of another dilator 300. The dilator 300 may include a shaft 306 having a proximal portion 302 and a tapered distal portion 304. The tapered distal portion 304 may be inserted into an opening in a subject's body. The dilator 300 may be inserted into the subject's body, and navigated to the target area, in a manner similar to the way the medical device 100 and the dilator 200 are inserted into and navigated through the subject's body.

A micropattern 310 may be disposed on the outer surface of the dilator 300. An enlarged view 312 of the micropattern 310 is shown in FIG. 3. The micropattern 310 may include protrusions 316 and gaps 314 similar to the protrusions 116 and gaps 114 of the micropattern 110, and the protrusions 216 and gaps 214 of the micropattern 210. As the dilator 300 is inserted through an opening, the tapered distal portion 304 may engage tissue around the opening. Insertion of the tapered distal portion 304 into the opening may dilate the opening, as larger diameter portions of the tapered distal portion 304 engage tissue around the opening. Engagement between the tapered distal portion 304 and the tissue may cause cells to transfer from the tissue to the outer surface of the dilator 300. The cells, or portions thereof, may be captured by the protrusions 316 and gaps 314.

Additionally or alternatively, the micropattern 310 may include the recesses 416 and gaps 414 shown in FIG. 4. The characteristics of the recesses 416 and gaps 414 has already been described above.

A source of electrical energy (not shown) may be coupled to the proximal portion 302 of the medical device 300. The electrical energy source may be configured to supply electrical current to the tapered distal portion 304 through the proximal portion 302. The electrical current may provide an electrical charge to the tapered distal portion 304, thereby changing a static charge on the tapered distal portion 304, to increase or decrease the gripping force between the cells and the tapered distal portion 304, and/or to increase or decrease attraction/repulsion forces between the protrusions 316, to cause them to move towards each other, or away from each other.

Embodiments of the present disclosure may be applicable to various and different medical or non-medical procedures. In addition, certain aspects of the aforementioned embodiments may be selectively used in collaboration, or removed, during practice, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A cytology brush, comprising:
   an elongated shaft including a proximal end portion and a distal end portion; and
   a plurality of elongated bristles each having a longitudinal axis, the plurality of elongated bristles mounted on the distal end portion of the elongated shaft with the longitudinal axis of each bristle extending radially away from the elongated shaft, the plurality of bristles being arranged at least partially around the distal end portion of the elongated shaft and configured to engage tissue;

wherein an outer surface of one of the plurality of bristles includes a micropattern formed by a plurality of protrusions or recesses extending radially outward or inward from the outer surface of the bristle, separated by one or more gaps, wherein the plurality of protrusions or recesses are arranged in longitudinally extending columns separated by the one or more gaps, or the plurality of protrusions or recesses are arranged in circumferentially extending rows separated by the one or more gaps.

2. The cytology brush of claim 1, wherein the plurality of protrusions or recesses have one of a rectangular or circular cross-sectional shape.

3. The cytology brush of claim 1, wherein the protrusions or recesses have a width between 10 and 20 micrometers, and each of the one or more gaps has a width of between 10 and 20 micrometers.

4. The cytology brush of claim 1, wherein the micropattern is configured to exert a holding force on cells from the tissue when the plurality of bristles engage the tissue.

5. The cytology brush of claim 1, wherein the plurality of bristles are helically arranged around the distal end portion of the elongated shaft.

6. The cytology brush of claim 1, wherein the plurality of bristles are made of at least one filament.

7. The cytology brush of claim 6, wherein the at least one filament includes a multicomponent filament, the multicomponent filament including a core surrounded by one or more layers arranged concentrically around the core.

8. The cytology brush of claim 6, wherein the at least one filament includes a monofilament.

9. The cytology brush of claim 6, wherein the at least one filament is made of at least one of nylon and a polymer.

10. A medical device, comprising:
a cytology brush, including:
an elongated shaft including a proximal end portion and a distal end portion, and
a plurality of elongated bristles each having a longitudinal axis, the plurality of elongated bristles mounted on the distal end portion of the elongated shaft with the longitudinal axis of each bristle extending radially away from the elongated shaft, the plurality of bristles being arranged at least partially around the distal end portion of the elongated shaft and configured to engage tissue, wherein an outer surface of one of the plurality of bristles includes a micropattern formed by a plurality of protrusions or recesses extending radially outward or inward from the outer surface of the bristle, separated by one or more gaps, wherein the plurality of protrusions or recesses are arranged in longitudinally extending columns separated by the one or more gaps, or the plurality of protrusions or recesses are arranged in circumferentially extending rows separated by the one or more gaps; and a sheath including a central lumen and a distal end opening, wherein the central lumen is configured to receive at least a portion of the cytology brush, and at least a portion of the cytology brush is configured to pass through the distal end opening.

11. The medical device of claim 10, wherein the plurality of protrusions or recesses are arranged in longitudinally extending columns separated by the one or more gaps, and are arranged in circumferentially extending rows separated by the one or more gaps.

12. The medical device of claim 10, wherein the protrusions or recesses have a width between 10 and 20 micrometers, and each of the one or more gaps has a width of between 10 and 20 micrometers.

13. The medical device of claim 10, wherein the micropattern is configured to exert a holding force on cells from the tissue when the plurality of bristles engage the tissue.

14. The medical device of claim 10, wherein the plurality of bristles are helically arranged around the distal end portion of the elongated shaft.

15. The cytology brush of claim 1, wherein the outer surface of each of the plurality of bristles includes the micropattern formed by a plurality of protrusions or recesses, separated by one or more gaps.

16. The medical device of claim 10, wherein the outer surface of each of the plurality of bristles includes the micropattern formed by a plurality of protrusions or recesses, separated by one or more gaps.

* * * * *